United States Patent [19]

Watson et al.

[11] 4,443,643
[45] Apr. 17, 1984

[54] REACTION OF BENZENE WITH ETHYLENE OXIDE TO PRODUCE STYRENE

[75] Inventors: James M. Watson; Cleve Forward, both of Big Spring, Tex.

[73] Assignee: Cosden Technology, Inc., Dallas, Tex.

[21] Appl. No.: 497,378

[22] Filed: May 23, 1983

[51] Int. Cl.³ .............................................. C07C 1/20
[52] U.S. Cl. .................................... 585/437; 585/454
[58] Field of Search ................ 585/437, 440, 444, 454

[56] References Cited

U.S. PATENT DOCUMENTS 3,403,193 9/1968 Russell ................................ 585/437
3,442,963 5/1969 Korchak ............................. 585/437
3,748,251 7/1973 Demmel et al. ..................... 208/120

Primary Examiner—Delbert E. Gantz
Assistant Examiner—Anthony McFarlane
Attorney, Agent, or Firm—Russell H. Schlattman; M. Norwood Cheairs

[57] ABSTRACT

A process for the production of styrene wherein ethylene oxide and benzene are added to a reactor at a temperature between about 600° F. and about 825° F. in the presence of an aluminosilicate type catalyst. The reaction proceeds directly to form styrene within the reactor.

1 Claim, No Drawings

REACTION OF BENZENE WITH ETHYLENE OXIDE TO PRODUCE STYRENE

BACKGROUND OF THE INVENTION

The present invention relates to a process for producing styrene. More particularly, the present invention involves a process for the direct production of styrene by passing ethylene oxide and benzene over an aluminosilicate catalyst.

Historically, styrene has been produced in a two step process including a first step for the alkylation of benzene to form ethylbenzene and a second step wherein ethylbenzene is dehydrogenated to styrene. A common method for the formation of ethylbenzene is the addition of ethylene to benzene in the presence of a alkylation catalyst. In U.S. Pat. No. 3,251,897 by Wise, ethylbenzene is formed by the alkylation of benzene with ethylene over a rare earth exchange aluminosilicate catalyst at temperatures below 600° F.

In U.S. Pat. No. 3,751,506 by Burress, benzene is alkylated with ethylene in the presence of a zeolite ZSM-5 catalyst to produce a mixture of ethylbenzene, diethylbenzene and triethylbenzene.

It should be appreciated therefore that the a two step process requiring an alkylation step to produce ethylbenzene and then a dehydrogenation step to produce styrene could be greatly simplified if styrene were produced directly. In addition to simplifying the overall process, direct production of styrene will result in decreased process time and process costs over the other two step processes.

SUMMARY OF THE INVENTION

There is therefore provided in accordance with the present invention, a direct process for producing styrene. The process comprises reacting ethylene oxide with benzene under conversion conditions in the presence of an aluminosilicate catalyst. Conversion conditions under the present invention involve reacting ethylene oxide and benzene in the presence of an aluminosilicate catalyst at a reactor inlet temperature between about 600° F. and about 825° F., a reactor inlet pressure from about 50 psig to about 100 psig, and a LHSV from about 1 to about 15. The preferred reactor inlet temperature is from about 675° F. to about 800° F.

DETAILED DESCRIPTION OF THE INVENTION

The present invention includes a direct process for producing styrene comprising reacting ethylene oxide with benzene under conversion conditions in the presence of a aluminosilicate catalyst. By a direct process it is meant that ethylene oxide and benzene are reacted under conditions comprising a single reactor inlet temperature, single reactor inlet pressure, and a single catalyst to form styrene and other products. Direct process reaction conditions include straight flow-through of products with no flow disruption between the initial benzene/ethylene oxide feed and the styrene end product. Although not wishing to be bound by theory, it is believed the reaction proceeds by a phenylethylalcohol intermediate which is dehydrated in situ to styrene.

Conversion conditions include a reactor inlet temperature from about 600° F. to about 825° F. The preferred reactor temperature range is from about 675° F. to about 800° F. At temperatures below 550° F., little or no ethylbenzene, xylene or styrene is formed. At temperatures above 1000° F., little or no styrene is found. It has been found, however, that as the temperature increases, the rate of reaction to styrene and other alkylaromatic products increases.

The reactor inlet pressure may range from about 55 psig to about 100 psig. A preferred pressure range is from about 55 psig to about 60 psig. It has been found that an increased inlet pressure improves catalyst stability thereby increasing the cycle times between regeneration. Further reactor conditions include a liquid hourly space velocity (LHSV) defined as the volume of ethylene oxide and benzene feed per volume of catalyst per hour, from about 1 to about 32. The preferred LHSV is from about 5 to about 7.2. Conversion conditions also include a molar ratio of benzene to ethylene oxide from about 1:1 to about 10:1.

The process of the present invention can be carried out using a variety of process equipment including a reactor vessel having a conversion zone which contains the aluminosilicate material. Either a fixed bed, moving bed or fluidized bed can be utilized. After a controlled velocity through the reaction zone, the converted product passes out of the reactor for recovery or separation utilizing standard techniques well known in the art.

The reaction proceeds in a reactor containing a bed of aluminosilicate catalyst. It is preferred that the reactor contain an aluminosilicate large pore zeolite type catalyst. It is most preferred that a Type Y molecular sieve zeolite catalyst be utilized. The composition and preparation of the Type Y molecular sieve zeolite is disclosed in U.S. Pat. No. 3,549,557 by Pickert et al, which is incorporated herein by reference in its entirety. The catalyst of the present invention is prepared from a synthetic crystalline zeolite Y; the preparation and composition of which is disclosed in U.S. Pat. No. 3,130,007, which is also incorporated by reference herein in its entirety.

Although the catalyst used in the process of the present invention is subject to some coking, it is possible to regenerate the catalyst by passing oxygen across the catalyst bed at reactor temperatures for approximately three hours.

The following examples are provided to illustrate the invention, however, are not intended to be limitative of the invention.

EXAMPLE 1

A cylindrical reactor is utilized having a diameter of ½ inch and a length of approximately 42 inches. A type Y molecular sieve zeolite described previously and further identified as Catalyst SK500, a product of Union Carbide Company, was utilized. The reactor bed depth was approximately eight inches. A mixture of benzene and ethylene oxide was pumped into the inlet end of the reactor at various molar ratios and at various LHSV's shown below. An excess amount of $N_2$ was also added into the reactor to stabilize the ethylene oxide against the high reactor temperature. The inlet temperature was maintained as shown below. The inlet pressure was maintained at 55 psig. At the discharge end of the reactor, the reaction products were collected and analyzed by gas liquid chromatography. The results are as indicated in Table I.

TABLE I

| °F. | LHSV | Molar Ratio Benzene/BO | % Conv. (1) | % by Weight of Products | | Selectivity (2) |
| --- | --- | --- | --- | --- | --- | --- |
| | | | | Alkyl Aromatics | STY | |
| 750° | 7.2 | 5.6/1.0 | 7.1 | 6.3 | 0.3 | 4.2 |
| 550° | 7.2 | 5.6/1.0 | 2.8 | 2.8 | — | — |
| 750° | 7.2 | 5.6/1.0 | 2.4 | 2.2 | 0.1 | 4.2 |
| 780° | 14.8 | 4/1.0 | 4.2 | 3.8 | 0.4 | 9.5 |
| 780° | 7.2 | 6.2/1.0 | 7.5 | 5.7 | 0.9 | 12.0 |
| 1000° | 8.0 | 14.6/1.0 | 4.5 | 4.6 | — | — |
| 1000° | 5.0 | 7.5/1.0 | 6.2 | 6.2 | — | — |

All Runs at 55 psig.
(1) Based upon weight percentage of total alkylated aromatics (including toluene, ethylbenzene, xylene and styrene) and unidentified heavy products to benzene in feed.
(2) Based upon weight percentage of styrene to total alkylated aromatics and unidentified heavy products.

The temperature dependence of the reaction can be seen in the above data wherein at 550° F. and 1000° F., no styrene was found.

Although several specific embodiments of the present invention have been described in the detailed description above and in the examples, this description is not intended to limit the invention to the particular form or embodiments disclosed herein since they are to be recognized as illustrative rather than limitative, and it will be obvious to those skilled in the art that the invention is not so limited. Thus, the invention is declared to cover all changes and modifications of the specific examples of the invention herein disclosed for purposes of illustration which do not constitute departure from the spirit and scope of the invention.

The embodiments of the invention in which an exclusive property or privilege is claimed is defined as follows:

1. A one step process for producing styrene comprising reacting ethylene oxide with benzene under conversion conditions in the presence of an an aluminosilicate, large pore, Type Y molecular sieve zeolite catalyst, wherein the conversion conditions comprise:
   (a) a reactor inlet temperature from about 600° F. to about 825° F.;
   (b) a reactor inlet pressure from about 50 psig to about 100 psig
   (c) a liquid hourly space velocity from about 1 to about 15; and
   (d) a molar ratio of benzene to ethylene oxide from about 1:1 to about 10:1.

* * * * *